United States Patent [19]

Stephan et al.

[11] Patent Number: 4,550,207

[45] Date of Patent: Oct. 29, 1985

[54] PROCESS FOR THE PREPARATION OF BENZENE COMPOUNDS

[75] Inventors: Günter Stephan, Bergisch-Gladbach; Karl Heinz Schündehütte, Leverkusen, both of Fed. Rep. of Germany

[73] Assignee: Bayer Aktiengesellschaft, Leverkusen, Fed. Rep. of Germany

[21] Appl. No.: 774,453

[22] Filed: Mar. 4, 1977

[30] Foreign Application Priority Data

Mar. 8, 1976 [DE] Fed. Rep. of Germany ....... 2609530

[51] Int. Cl.$^4$ ............................................ C07C 109/04
[52] U.S. Cl. .................................. 564/311; 562/439; 564/312; 260/510
[58] Field of Search ............... 260/569, 578, 580, 510; 564/311, 312; 562/439; 260/510

[56] References Cited

U.S. PATENT DOCUMENTS

| | | | |
|---|---|---|---|
| 1,589,936 | 6/1926 | Brown et al. | 260/569 |
| 2,233,128 | 2/1941 | Henke et al. | 260/569 |
| 2,640,081 | 5/1953 | Farkos et al. | 564/312 |
| 3,063,980 | 11/1962 | Bloom et al. | 260/569 |
| 3,361,819 | 1/1968 | Kosak et al. | 260/580 |

OTHER PUBLICATIONS

Furst et al., *J. Am. Chem. Soc.* 79, 5492–5493 (1957).
Hornsby et al., *Chem. & Ind.* 1958, 858–859.
Abdrakhmanova et al., *Chem. Abstr.* 76, 45498d (1972).
Dzhardamalieva et al., *Chem. Abstr.* 53, 271i (1959).
Tarama et al., *Chem. Abstr.* 55, 21752h (1961).
Houben-Weyl, "Methoden der Organischen Chemie", vol. X, 2, pp. 721–724 (1967).

*Primary Examiner*—Robert V. Hines
*Attorney, Agent, or Firm*—Sprung Horn Kramer & Woods

[57] ABSTRACT

The reduction of azoxybenzene, azobenzenes and mixtures of azoxybenzenes and azobenzene to the hydrazobenzenes is possible under mild conditions, with high yields and without any great excess of reducing agents in the presence of raney-nickel and compounds which have an alkaline action with hydrogen or hydrazine hydrate.

9 Claims, No Drawings

PROCESS FOR THE PREPARATION OF BENZENE COMPOUNDS

The subject of the invention is an improved process for the preparation of hydrazobenzene and its derivatives from the corresponding azoxybenzenes, azobenzenes or mixtures of azobenzenes and azoxybenzenes by reduction with hydrogen or hydrazine in the presence of Raney nickel.

A further subject of the invention is a process for the preparation of 4,4'-diaminodiphenyl compounds by reduction of azoxybenzenes, azobenzenes or mixtures of azobenzenes and azoxybenzenes with hydrogen or hydrazine in the presence of Raney nickel and subsequent rearrangement of the hydrazobenzenes thus obtained, without intermediate isolation thereof.

Diaminodiphenyl compounds are in a dominant position as tetrazo components for the preparation of disazo and polyazo dyestuffs which are soluble in water and sparingly soluble in water.

The preparation of these compounds always starts from nitrobenzene or substituted nitrobenzenes and these compounds are reacted with very diverse reducing agents, optionally with isolation of intermediate stages, such as azoxybenzenes, to give the corresponding hydrazobenzenes and these, in turn, are rearranged under the action of an aqueous mineral acid to give the desired tetrazo components.

Many proposals have already been made for this reduction process; a comparative review is given in Houben-Weyl, Methoden der organischen Chemie (Methods of Organic Chemistry), volume X/2. The known reduction processes can be divided into four groups; (1) reduction with metals, for example the process with zinc in the presence of alkali, which is widely used industrially at present, (2) electrochemical reduction processes, (3) reduction with non-metallic reducing agents, such as formaldehyde, and (4) catalytic hydrogenation.

The reduction processes can be carried out both as single stage processes and as two-stage processes, for example with isolation of the azoxy compounds which are formed as intermediates, or of mixtures of azoxy compounds and azo compounds which are formed as intermediates, and it is possible to use the same reducing agent or different reducing agents in the two reduction stages.

The processes which work with metals and for which, in addition to zinc, iron, iron aluminium alloys and sodium amalgam have been proposed require high investment for working up the reducing agents.

Electrochemical reduction processes are very expensive from the point of view of apparatus and require a great deal of energy.

Reduction processes which use methanol, sodium sulphide of formaldehyde as the reducing agent give stoichiometric amounts of by-products which are not always desired or, as in the case of sodium sulphide, are avoided on the plant for reasons of occupational health.

A common feature of all of these processes is that the hydrazobenzene has to be isolated before it is rearranged with mineral acid to give the diaminodiphenyl derivative.

In order to eliminate the difficulties or disadvantages of the abovementioned processes, it has already been proposed (Houben-Weyl, volume X/2, pages 721 to 724) to reduce azo compounds and azoxy compound catalytically to hydrazo compounds, catalysts which are used being palladium-on-calcium carbonate, palladium-on-charcoal, ruthenium-on-charcoal and platinum-IV oxide. In addition to molecular hydrogen, hydrazine hydrate can also be used as the source of hydrogen. The reduction reactions generally proceed under mild conditions. Nevertheless the danger of over-reduction to the corresponding anilines is great, compare, for example, Methodicum Chimicum, volume VI, 6. Aromatische Hydrazoverbindungen (Aromatic Hydrazo Compounds), page 161, Georg Thieme Verlag, Stuttgart, 1974.

However, Raney nickel is to be preferred for reasons of economy. It is true that reduction with Raney nickel has already been proposed (J. Am. Chem. Soc. 78, 5445 (1956), J. Am. Chem. Soc. 79, 5492 (1957) and U.S. Pat. No. 1,589,936) but this does not proceed under mild conditions as is the case with the expensive catalysts already mentioned. Thus, it is stated in U.S. Pat. No. 1,589,936 that the reduction must be carried out at 100° C. It is necessary to maintain this temperature accurately since even at 126° C. it is no longer the desired hydrazo compound which is obtained but, virtually quantitatively, the corresponding aniline and at 80° C. hardly any hydrazobenzene is produced, even after a longer reaction time, but, in the main, the starting material is recovered. Even poorer results are described in J. Am. Chem. Soc. 56, 1411 to 1412 (1934). In this case azobenzene is reduced to aniline in good yield in the presence of a nickel catalyst at 99° C. If the reduction is stopped after one mol of hydrogen has been consumed per mol of azobenzene, a mixture of hydrazobenzene, aniline and unchanged azobenzene is found. If the temperature is lowered to 55° C., the absorption of hydrogen is greatly slowed down and aniline is formed in preference to hydrazobenzene. The reduction of nitrobenzene to yield hydrazobenzene with hydrogen in the presence of a nickel catalyst in aqueous alkali is described in U.S. Pat. No. 2 194 938. The product is a mixture of hydrazobenzene, azobenzene and aniline which has to be reduced further. The process proceeds so badly that after the conversion of hydrazobenzene to benzidine still remaining azobenzene has to be further reduced with iron and hydrochlorine acid and finally converted.

A technical application of this method is impossible in view of the laborious process steps.

If hydrogen is replaced as the reducing agent by hydrazine hydrate, high concentrations of the latter reducing agent must be used in order to obtain the hydrazo compounds. If only for reasons of safety, it is not permissible to carry out the reduction with anhydrous hydrazine, as is proposed in J. Am. Chem. Soc. 78, 5446 (1956), in a large scale industrial plant since anhydrous hydrazine is extremely explosive.

With the process according to the invention it is now possible, surprisingly, to carry out the reduction of azoxybenzenes, azobenzenes and mixtures of azoxybenzenes and azobenzenes under mild conditions and without any great excess of reducing agents in the presence of Raney nickel. The process according to the invention for the preparation of hydrazobenzenes from azoxybenzenes, azobenzenes and mixtures of azoxybenzenes and azobenzenes by catalytic reduction with hydrogen or hydrazine hydrate in the presence of Raney nickel is characterised in that it is carried out in aqueous or nonaqueous lower alcohols wherein the amount of water is at most 50% by weight, preferably 30% of the total solvent in the presence of alkali metal compounds and alkaline earth metal compounds which have an alkaline action or of ammonia or organic bases.

Completely unexpectedly, the desired reduction proceeds readily and rapidly, and with high yields, under these conditions at temperatures between 20° and 100° C. and preferably between 60° and 80° C.

Suitable lower alcohols are for example methanol, ethanol, isopropanol and glycol monomethyl ether.

The process is especially suitable for the preparation of hydrazobenzenes of the following formula:

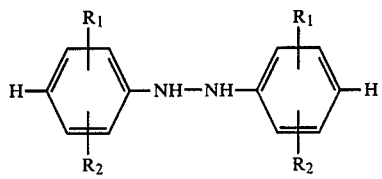

wherein $R_1$ and $R_2$ denote hydrogen, amino, $C_1-C_4$-alkyl, $C_1-C_4$-alkoxy which is optionally substituted by carboxyl, carboxyl, sulpho or halogen, preferably hydrogen, methyl, methoxy or chlorine.

The preparation, by this route, of the chlorine-substituted hydrazobenzenes in particular was not to be expected from the literature since, according to F. Zymalkowski, Katalytische Hydrierungen im organisch-chemischen Labor (Catalytic Hydrogenations in an Organic Chemistry Laboratory), Ferdinand Enke Verlag, Stuttgart (1965), pages 161 to 170, dehalogenations would have to be expected when catalytic hydrogenations are carried out in an alkaline medium. This fear is supported by the statement in J. Am. Chem. Soc. 62, 1687 to 1693 (1940) that, although chlorine atoms remain intact during the reduction of azo compounds in a neutral solvent, dehalogenation takes place, however, in the presence of alkali.

The process according to the invention is preferably carried out with hydrogen.

Examples of suitable alkali metal compounds and alkaline earth metal compounds which have an alkaline action are alkali metal hydroxides and carbonates and alkaline earth metal hydroxides and carbonates, such as sodium hydroxide, potassium hydroxide, lithium hydroxide, barium hydroxide, sodium carbonate and potassium carbonate. Organic bases which can be used are, for example, mono-, di- and tri-alkylamines as well as the corresponding ammonium compounds, piperidine, morpholine, quinoline, pyridine, diazabicyclooctane and 1,5-diazabicyclo[4.3.0]non-5-ene. Preferred compounds having an alkaline action are alkali metal hydroxides and alkaline earth metal hydroxides, especially sodium hydroxide, potassium hydroxide and barium hydroxide. The amount of alkali can be varied within wide limits and is not critical for the process according to the invention. Once the alkali has been introduced, virtually none of it is consumed during the reaction.

In theory, two mols of hydrogen or one mol of hydrazine hydrate are required per mol of azoxy compound to be reduced and one mol of hydrogen or half a mol of hydrazine hydrate is required per mol of azo compound to be reduced. In practice, hydrogen can be employed in an excess of up to 10% without any significant over-reduction occurring. With hydrazine hydrate over-reduction does not occur even with larger excesses but for economic reasons an excess of 20% is completely adequate to compensate for losses of hydrazine hydrate due to side reactions.

The amount of Raney nickel can vary within wide limits; in general it suffices to use 0.1 to 5 g per mol of the azo or azoxy compound to be reduced. With larger amounts the danger of over-reduction exists. The catalyst is prepared according to customary processes, such as those to be found in the relevant textbooks.

The azoxybenzenes, azobenzenes or mixtures of azoxybenzenes and azobenzenes which are necessary as starting materials can be obtained from nitrobenzenes by the known reduction processes. The starting materials used for the process according to the invention were preferably prepared by reduction with formaldehyde in aqueous NaOH, according to German Auslegeschrift (German Published Specification) No. 1,029,005.

A further subject of the invention is the preparation of 4,4'-diaminodiphenyl derivatives by reduction of azoxybenzenes, azobenzenes or mixtures of azoxybenzenes and azobenzenes by the process according to the invention and rearrangement, by the action of mineral acids, of the hydrazo compounds which are formed as intermediates, without isolation thereof. Mineral acids which can be used are the acids customarily used for the so-called benzidine rearrangement, for example hydrochloric acid or sulphuric acid.

EXAMPLE 1

53.4 g of 2,2'-dichloroazoxybenzene are stirred in 60 ml of methanol. 0.6 g of sodium hydroxide and 11.8 ml of hydrazine hydrate are added and the mixture is warmed to 65° C. After Raney nickel has been added (a total of about 0.05 g in 2-3 portions) vigorous evolution of nitrogen starts. The reduction has ended after 30 minutes. The mixture is cooled to 10° C. and diluted with water and the 2,2'-dichlorohydrazobenzene which has crystallised out is filtered off and washed with water until neutral. After the rearrangement to 3,3'-dichlorobenzidine and tetrazotisation with nitrous acid, a yield of 86% of theory is obtained.

Without the addition of sodium hydroxide only 36% of theory of 2,2'-dichlorohydrazobenzene are obtained.

EXAMPLE 2

53.4 g of 2,2'-dichloroazoxybenzene and 1.2 g of sodium hydroxide in 140 ml of methanol together with 11.3 ml of hydrazine hydrate are warmed to 65° C. After 0.05 g of Raney nickel has been added, vigorous evolution of nitrogen occurs and the temperature rises to 76° C. The reduction has ended after 1 hour. No further 2,2'-dichloroazoxybenzene can be detected in the pale, clear solution by chromatography.

If the reaction is carried out without sodium hydroxide, the evolution of nitrogen is only moderate and approximately 20% of 2,2'-dichloroazoxybenzene are still present in the reaction mixture after a reaction time of 6 hours.

EXAMPLE 3

If 53.4 g of 3,3'-dichloroazoxybenzene are reduced in the manner described in Example 1,93% of theory of 3,3'-dichlorohydrazobenzene are obtained after a reaction time of 30 minutes.

However, if the reaction is carried out without the addition of sodium hydroxide the yield of 3,3'-dichlorohydrazobenzene is only 53% of theory.

EXAMPLE 4

11 ml of water, 1.5 g of sodium hydroxide and 0.25 g of Raney nickel are added to 53.4 g of 2,2′-dichloroazoxybenzene in 160 ml of methanol. The hydrogenation reaction is carried out at 65° C. and under a hydrogen pressure of 10 bars. After a reaction time of about 1 hour the pressure remains constant. The mixture is cooled to 10° C. and diluted with 100 ml of water and the product is isolated by filtration. The yield of 2,2′-dichlorohydrazobenzene is 88% of theory.

Without sodium hydroxide, virtually no hydrogen is taken up.

EXAMPLE 5

1.2 g of sodium hydroxide and 0.25 g of Raney nickel are added to a suspension of 53.4 g of 3,3′-dichloroazoxybenzene in 60 ml of methanol and 15 ml of water and the hydrogenation reaction is carried out under a hydrogen pressure of 10 bars. After 90 minutes the mixture is cooled to 10° C. and the product is isolated by filtration. 3,3′-Dichlorohydrazobenzene is obtained in a yield of 89% of theory.

If the reaction is carried out under the same conditions but without sodium hydroxide, the hydrogen taken up amounts to at most 17% of theory.

EXAMPLE 6

Reduction of 45.2 g of 2,2′-dimethylazoxybenzene in accordance with the instructions given in Example 1 gives 2,2′-dimethylhydrazobenzene in a yield of 70% of theory.

Without sodium hydroxide, only 20% of theory are obtained under otherwise identical conditions.

EXAMPLE 7

0.6 g of sodium hydroxide and 11.8 ml of hydrazine hydrate are added to 53.4 g of 2,2′-dichloroazoxybenzene in 60 ml of methanol. The mixture is warmed to 65° C. and a total of 0.05 g of Raney nickel is added. When the reduction has ended, 16 ml of water are added and the mixture is cooled to room temperature. 29.3 ml of sulphuric acid (60° Bè) are added dropwise in the course of 45 minutes at such a rate that a temperature of 50° C. is reached towards the end of the period of dropwise addition. The mixture is now stirred at this temperature until rearrangement is complete and is then heated to the boil. It is cooled to 10° C., the product is isolated and the residue is washed with highly dilute sulphuric acid until it is free from by-products which can be diazotised. In this way pure 3,3′-dichloro-4,4′-diaminodiphenyl sulphate is obtained in a yield of 80% of theory.

EXAMPLE 8

53.4 g of 3,3′-dichloroazoxybenzene are reduced as described in Example 7. The reaction mixture is then cooled to 40° C. and 37.2 ml of sulphuric acid (60° Bè) are allowed to run in in the course of 45 minutes at a temperature of 40°–45°. The mixture is further stirred at this temperature until the rearrangement is complete. A total of 40 ml of water is gradually added at intervals. When the rearrangement is complete, a further 35 ml of water are added and the mixture is heated to the boil. After cooling to 20° C., the product is isolated by filtration and washed with water containing sulphuric acid. The yield of 2,2′-dichloro-4,4′-diamino-diphenyl sulphate is 90% of theory.

EXAMPLE 9

267 g of 2,2′-dichloroazoxybenzene, in 350 ml of methanol, 100 ml of 40% strength by volume sodium hydroxide solution and 80 ml of water, are hydrogenated in the presence of 1.2 g of Raney nickel at 65° C. and under a hydrogen pressure of 10 bars. When about 105% of theory of hydrogen have been taken up, the reduction is complete. The mixture is cooled to 30° C. and 193 ml of sulphuric acid (60° Bè) are allowed to run in at such a rate that a temperature of 45°–50° C. is reached at the end of the addition. The mixture is further stirred at 50° C. until the rearrangement is complete, water is then added to make up to a total volume of 1 l and the mixture is heated to the boil. After cooling to 20° C., the mixture is filtered and the filtration residue is washed with a total of 600 ml of water, which also contain 5 ml of sulphuric acid (60° Bè), in 3 portions. Pure 3,3′-dichloro-4,4′-diaminodiphenyl sulphate is obtained in a yield of 72.5% of theory.

EXAMPLE 10

153 of o-nitroanisole are added dropwise to a mixture of 270 ml of methanol, 90 g of sodium hydroxide and 2 g of 2,3-dichloro-1,4-naphthoquinone at 55°–60° C., whilst stirring. After the exothermic reaction to give 2,2′-dimethoxyazoxybenzene has subsided, the mixture is stirred for a further 4 hours at 55°–60° C. and then cooled to 50° C. and 30 g of hydrazine hydrate are added. A total of 0.3 g of Raney nickel is added in several portions in such a way that a temperature of 45°–50° C. is maintained. When the reaction has ended, the mixture is cooled to 20° C. and the product is isolated by filtration and washed with water until neutral. The yield of 2,2′-dimethoxyhydrazobenzene is 95% of theory.

EXAMPLE 11

If, in Example 10, hydrogen under a pressure of 10 bars, in the presence of 0.6 g of Raney nickel, is used in place of hydrazine hydrate, an otherwise identical procedure gives 2,2′-dimethoxyhydrazobenzene in a yield of 95% of theory.

EXAMPLE 12

45.2 g of 2,2′-dimethylazoxybenzene are reduced as described in Example 6. The reaction mixture is cooled to room temperature and 37 ml of sulphuric acid (60° Bè) are allowed to run in slowly dropwise. The mixture is then stirred until the rearrangement is complete. The product is then filtered off and washed with 100 ml of 1% strength sulphuric acid. The yield of 3,3′-dimethyl-4,4′-diaminodiphenyl sulphate is 70% of theory.

We claim:

1. Process for the preparation of hydrazobenzenes from azoxybenzenes by catalytic reduction with hydrogen or hydrazine hydrate in the presence of 0.1–5 g of Raney nickel per mol of the azoxy compound characterized in that the reduction is carried out in aqueous or non-aqueous lower alcohols wherein the amount of water is at most 50% by weight, in the presence of a material selected from the group consisting of alkali metal hydroxides and alkaline earth metal hydroxides further characterized in that hydrazobenzenes of the formula

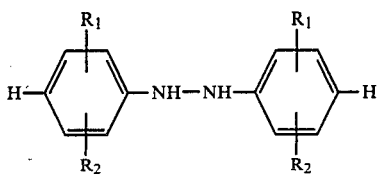

wherein

R$_1$ denotes hydrogen, amino, C$_1$-C$_4$-alkyl, C$_1$-C$_4$-alkoxy which is optionally substituted by carboxyl; carboxyl, sulpho or halogen and R$_2$ denotes amino, C$_1$-C$_4$-alkyl, C$_1$-C$_4$-alkoxy which is optionally substituted by carboxyl; carboxyl sulpho or halogen, are prepared from the corresponding azoxybenzenes.

2. A process according to claim 1 wherein in the hydrazobenzene:

R$_1$ denotes hydrogen, methyl, methoxy or chlorine and

R$_2$ denotes methyl, methoxy or chlorine.

3. A process according to claim 1 wherein the reduction is carried out at a temperature between 20° and 100° C.

4. A process according to claim 1 wherein the reduction is carried out at a temperature between 60° and 80° C.

5. Process according to claim 1, characterised in that the reduction is carried out in the presence of sodium hydroxide, potassium hydroxide or barium hydroxide.

6. Process according to claim 1, characterised in that hydrogen is used as the reducing agent.

7. Process according to claim 1, characterised in that hydrazobenzenes wherein

R$_1$ and R$_2$ denote hydrogen, methyl, methoxy or chlorine, are prepared.

8. Process according to claim 1, characterised in that hydrazobenzenes wherein

R$_1$ denotes hydrogen or chlorine and

R$_2$ denotes chlorine are prepared.

9. Process for the preparation of 4,4'-diaminodiphenyl derivatives by reduction of azoxybenzenes, by the process according to claim 1 and rearrangement of the reaction products by the action of mineral acids, characterised in that the hydrazo compounds which are formed as intermediates are not isolated.

* * * * *